United States Patent [19]

Gaffar et al.

[11] 4,183,915

[45] Jan. 15, 1980

[54] STABLE SOLUTION FOR DENTAL REMINERALIZATION

[75] Inventors: Maria C. S. Gaffar; Abdul Gaffar, both of Somerset, N.J.

[73] Assignee: Colgate-Palmolive Company, New York, N.Y.

[21] Appl. No.: 951,893

[22] Filed: Oct. 13, 1978

[51] Int. Cl.$^2$ .................... A61K 7/16; A61K 7/18; A61K 7/22
[52] U.S. Cl. .................................. 424/52; 424/49; 424/54; 424/57
[58] Field of Search .................................. 424/49-58

[56] References Cited

U.S. PATENT DOCUMENTS

| | | | |
|---|---|---|---|
| Re. 29,182 | 4/1977 | McCune et al. | 424/49 |
| 3,288,846 | 11/1966 | Irani et al. | 260/502 P |
| 3,298,956 | 1/1967 | Irani et al. | 260/502 P |
| 3,336,221 | 8/1967 | Ralston | 260/502 P |
| 3,434,969 | 3/1969 | Ralston | 260/502 P |
| 3,625,569 | 2/1972 | Medcalf | 424/48 |
| 3,671,644 | 6/1972 | Irani et al. | 424/329 |
| 3,792,152 | 2/1974 | Kim | 423/311 |
| 3,832,396 | 8/1974 | Irani et al. | 260/502 P |
| 4,097,588 | 6/1978 | Levine | 424/52 |
| 4,110,429 | 8/1978 | Gaffar et al. | 424/49 |

FOREIGN PATENT DOCUMENTS

| | | |
|---|---|---|
| 1617729 | 4/1971 | Fed. Rep. of Germany . |
| 1515665 | 3/1968 | France . |
| 2159507 | 5/1978 | France . |
| 1344815 | 5/1974 | United Kingdom . |
| 1394034 | 5/1975 | United Kingdom . |

OTHER PUBLICATIONS

Meyer and Nancollas Calc. Tiss. Res. 13:295–303 (1973), The Influence of Multi–Dentate Organo–Phosphonates on the Crystal Growth of Hydroxy Apatite.
Briner et al., Calc. Tiss. Res. 7:249–256 (1971), Factors Affecting the Rate of Post–Eruptive Maturation of Dental Enamel.
Monsanto Co. Brochure "Dequest" Organophosphorus Compounds, Feb. 1971.

*Primary Examiner*—Shep K. Rose
*Attorney, Agent, or Firm*—Robert L. Stone; Murray M. Grill; Herbert S. Sylvester

[57] ABSTRACT

An aqueous solution useful for remineralizing subsurface carious lesions of dental enamel which solution contains sources of calcium ions and phosphate ions as well as fluoride ions and further includes as an agent to stabilize the solution against precipitation, an antinucleating agent such as ethylenediamine tetramethylenephosphonic acid or water soluble salt thereof, the pH of the solution being about 5–9, preferably close to physiological conditions, such as about 6.8–7.5.

17 Claims, No Drawings

STABLE SOLUTION FOR DENTAL REMINERALIZATION

This invention relates to a stable aqueous solution which is effective to remineralize carious lesions in dental enamel.

It is known that dental caries begin with lesions of so-called "white spots," which are demineralized areas below the surface of intact dental enamel. If unchecked, surface enamel above a sub-surface lesion eventually collapses, leading to cavitation and subsequent loss of tooth structure.

In order to arrest demineralization, and, indeed, in order to remineralize "white spots" various compositions have been proposed. For instance, U.S. Pat. No. 3,679,360 to Rubin et al discloses deposition of calcium phosphate from a gel onto a tooth surface. This, however, does not reach the sub-surface area where demineralization initially occurs. Further, because of the difficulty of maintaining both calcium ions and phosphate ions available without precipitating a calcium phosphate material, two part kits have been proposed in which a calcium component and a phosphate component are sequentially applied to the oral cavity as in British Pat. No. 1,408,922 to Raff et al and British Pat. No. 1,452,125 to Grabenstetter et al or mixed together shortly before such application to form a metastable system with temporary stability as in U.S. Pat. No. 4,080,440 to DiGiulio et al and British Pat. No. 1,509,977 to Levine. Another metastable solution has been described in U.S. Pat. No. 4,097,588 to Levine. Even this solution, however, is not substantially permanent and precipitation can occur, particularly when fluoride ions are present.

It is an advantage of this invention that a one-part stable aqueous remineralizing solution is suitably prepared as a dental mouthrinse and also can be incorporated into other dentifrice compositions such as a dental cream or gel, mouth spray, troche, chewable tablet, lozenge and the like.

Further advantages will be apparent from consideration of the following specification.

In accordance with certain of its aspects, this invention relates to a stable aqueous remineralizing solution comprising water having dissolved therein a source of calcium ions and a source of phosphate ions, the amount of calcium ions and phosphate ions being sufficient to effect remineralization of dental enamel; a compound which provides fluoride anticaries agent; and an antinucleating agent selected from the group of acids and orally acceptable water-soluble salts thereof consisting of: diamine tetramethylenephosphonic acids of the formula $(M_2O_3PH_2C)_2N(CH_2PO_3M_2)_2$, wherein n is an integer from 1 to 10; phosphonoacetic acid or salt thereof of the formula $M_2O_3PCH_2COOM$; peroxydiphosphate of the formula $M_4P_2O_8$; an oligomer

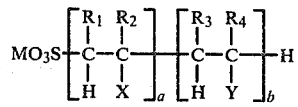

in which M is hydrogen or an orally acceptable cation; $R_1$, $R_2$, $R_3$, and $R_4$ are independently hydrogen, methyl or ethyl; Y is at least one hydrophilic member of the group consisting of COOM, —CONH$_2$ and CH$_2$OH; X is at least one hydrophobic member of the group consisting of —CN, —COOR, —COOR$_5$OR, —CONHR and COONHR$_5$COR; R is C$_{1-8}$ alkyl; R$_5$ is C$_{1-4}$ alkylene a is 0–7 and a+b is about 4–15; said solution having a pH of about 5 to about 9.

The antinucleating properties of the agents employed in the present invention appear to be effective to prevent precipitate formation from the calcium and phosphate ions of the solution particularly with the fluoride ions also present. As described in Ciba Foundation Symposium, "Hard Tissue Growth, Repair and Remineralization" (Elsevier), Associated Scientific Publishers, New York, 1973 in the article by Francis et al, "Chemical Agents in the Control of Calcification Processes in Biological Systems," pages 57–83, particularly at pages 75–78, an antinucleating agent (e.g., a diphosphonate) can in sufficient quantity at a physiological pH completely absorb onto a spherical nucleated particle of hydroxyapatite as it forms and entirely block crystal growth. In this way, the formation of large insoluble crystals of apatite is prevented and coated small hydroxyapatite crystals of higher water solubility are attained.

It has been found that not all antinucleating agents can successfully stabilize calcium ions and phosphate ions in solution against precipitating to form large insoluble apatite crystals. For instance, such insoluble crystals form when it is sought to use antinucleating agents such as sodium hexametaphosphate, sodium pyrophosphate, sodium phytate and mellitic acid as well as disodium phosphonoethane-1,2-dicarboxylate, 1,1-diphosphonopropane-2,3-dicarboxylic acid monohydrate, 3-amino-1-hydroxypropane-1,1-diphosphonic acid and imino-diacetic-N-methylene phosphonic acid. On the other hand, the antinucleating agents of the present invention successfully stabilize the calcium ions and phosphate ions against precipitation as large insoluble apatite crystals in solution at a pH between about 5 and about 9. Preferably, the pH is adjusted to about 6.8 to about 7.5, which approximates usual human physiological conditions and is optimum for effecting remineralization. Desirably, the antinucleating agent of the invention is present in amount of about 1 to 500 ppm ($1 \times 10^{-6}$M to $1 \times 10^{-3}$M) of the solution, preferably about 25 to 250 ppm ($5 \times 10^{-6}$M to $5 \times 10^{-3}$M), such as about 225 ppm ($5 \times 10^{-4}$M).

The antinucleating agent of the invention is desirably a diamine tetramethylenephosphonic acid of the formula $(M_2O_3PH_2C)_2N(CH_2)_n(CH_2PO_3M_2)_2$ wherein n is an integer from 1 to 10 and M is hydrogen or an orally acceptable cation such as alkali metal (e.g., sodium or potassium), ammonium or C$_1$–C$_{18}$ mono-, di- or trisubstituted ammonium (e.g., mono-, di- or tri-ethanolammonium) salt.

The polyamine polyphosphonic compounds which are most preferred are ethylenediamine tetra (methylenephosphonic acid), (hereinafter EDITEMPA) and its water-soluble orally acceptable salts, (e.g., sodium, potassium, and ammonium and other pharmaceutically acceptable salts; most preferably the tri-, tetra- or penta-sodium salts), other polyamine polyphosphonic compounds include: tetramethylenediamine tetra (methylenephosphonic acid), pentamethylene diamine tetra (methylenephosphonic acid), hexamethylenediamine tetra (methylenephosphonic acid) and the water-soluble salts of these acids, e.g., sodium, potassium, ammonium and other orally acceptable salts.

Phosphonoacetic acid (hereinafter PAA) and its water soluble orally acceptable salts are also desirable antinucleating agents. They are characterized by the formula $M_2O_3PCH_2COOM$, wherein M has the meaning indicated above.

The peroxydiphosphate (hereinafter PODP) and particularly the alkali metal salts thereof (e.g., potassium or sodium) are likewise desirable antinucleating agents. They are characterized by the formula $M_4P_2O_8$ wherein M has the meaning indicated above.

The desirable oligomer antinucleating agents and methods for their preparation are described in U.S. Pat. Nos. 3,646,099 and 3,859,260, the disclosures of which are incorporated herein by reference. They have the formula:

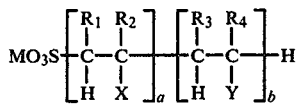

wherein

M is hydrogen or a water soluble orally acceptable cation (as indicated above);

$R_1$, $R_2$, $R_3$ and $R_4$ are independently H, methyl or ethyl;

Y is at least one hydrophilic member of the group consisting of —COOM, —COHN$_2$ and —CH$_2$OH;

X is at least one hydrophobic member of the group consisting of —CN, —COOR, —COOR$_5$OR, —CONHR and —COONHR$_5$COR, R is $C_{1-8}$ alkyl;

$R_5$ is $C_{1-4}$ alkylene;

a is 0–7; and a+b is about 4–15.

These oligomers are anionic and of relatively low and accurately regulated degree of polymerization, (in contrast to the conventional free radical redox polymerization conducted with an oxidative initiator such as hydrogen, alkyl, or acyl peroxides, persulfates or hydroperoxides in relatively large amounts and a reductive activator such as NaHSO$_3$, Na$_2$S$_2$O$_4$ or sodium formaldehyde sulfoxylate in relatively low amounts generally added subsequently to the polymerization medium) are prepared by a reductive polymerization in which a much larger amount of a bisulfite salt, e.g., NaHSO$_3$ (sodium bisulfite, sodium acid sulfite), a reducing agent, is the initiator charged initially with the monomer, and an oxidixing agent is added in smaller amounts as the activator during the polymerizing or oligomerizing process.

Subscript a in the formula represents the number of moles of hydrophobic groups, and subscript b the number of moles of hydrophilic groups, in the oligomer molecule. The proportion of X (i.e., the value of a) must be small enough, or even zero, to avoid the production of a too large, sticky and hydrophobic polymer molecule, and will of course be dependent for the most part in any particular instance on the identity of the X and Y groups, i.e., the hydrophobic-containing and hydrophilic containing monomeric reactants. Mixtures of such oligomers may of course also be employed.

Examples of monomers containing hydrophilic Y group are acrylic acid, methacrylic acid, alpha-ethylacrylic acid, beta-methylacrylic acid, alpha, beta-dimethylacrylic acid, orally acceptable salts of these acids, for example those containing such cations as alkali metal (e.g., sodium and potassium), ammonium, $C_{1-18}$ mono-, di- and tri-substituted ammonium (e.g., alkanol substituted such as mono-, di- and tri-ethanolammonium), etc., acrylamide, methacrylamide, ethacrylamide, and allyl alcohol and the like.

Examples of monomers containing hydrophobic X groups are acrylonitrile, methacrylonitrile, ethacrylonitrile, methyl and ethyl and octyl acrylate and methacrylate, methoxyethyl acrylate, octoxyethyl methacrylate, ethoxybutyl methacrylate, propoxymethyl acrylate, N-ethylacrylamide, N-isopropylacrylamide, N-methylacrylamide, N-propylethacrylamide, vinyl acetate, propionate and octanoate, diacetone acrylamide and the like.

The oligomerization is carried out in water in the presence of a relatively large amount of the bisulfite reducing initiator, expressed in mols of monomer/gram formula weight (gFW) of reducing initiator is about 4 to 15, this ratio determining the degree of oligomerization.

The reductive initiator is preferably a water soluble bisulfite salt (M in the formula), especially alkali metal, such as sodium or potassium, but bisulfite salts containing other orally acceptable cations of the type referred to above may be employed.

In practice, enough oxidative activator is used to effect 100% conversion of the monomers to oligomers. The amount of such activator, expressed as gFW activator/gFW initiator may range from 0.0001 to 0.1 but usually is from about 0.0001 to 0.1. Examples of these oxidative activators are ammonium, sodium potassium persulfate, hydrogen peroxide and other water soluble oxidants commonly employed in the polymerization art.

Following completion of the oligomerization reaction, any free carboxylic acids groups in the oligomer molecules may, if desired, be partially or completely neutralized, preferably at least 60%, by treating the aqueous oligomer solution with a suitable base to convert such groups to their salts with orally acceptable cations as referred to above. These aqueous oligomer solutions have a highly desirable low viscosity, and low molecular weight range depending on the monomer units in the oligomer.

It will be understood that the oligomer formula above is not intended to depict the actual structure of the oligomer molecule, the bracketed units of which formula are randomly distributed in the molecule with the —SO$_3$M group being normally bonded to a terminal carbon atom in the oligomer chain devoid of X and or Y substituents. In the oligomers preferred for use herein, a is zero, Y is —COOM, R$_1$–R$_4$ are H, and M is alkali metal, e.g., sodium, b being about 10, as derived from acrylic acid. An oligomer of the formula above in the form of its sodium salt, with a molecular weight of about 1,000, containing about 10 acrylic acid monomeric units, is commercially available under the trade name ND-2 (a product of UniRoyal).

The effective antinucleating agents render the remineralizing solution stable at normally occurring temperatures, e.g., about 15° C.–40° C. The remineralizing agents can diffuse effectively through an intact enamel surface in order to act on subsurface lesions.

The stability provided by the effective antinucleating agents prevents spontaneous precipitation on enamel surfaces and thereby permits diffusion of the remineralizing components to subsurface lesions.

One or more sources of each calcium ions and phosphate ions may be employed. When the source is normally insoluble such as a calcium phosphate, it is solubilized during preparation of the solution, by maintaining an acid pH of about 6 or less (e.g., about 2.5 to 6) during preparation of the remineralizing solution, particularly before the effective antinucleating agent is added.

The insoluble sources of calcium and phosphate ions may be a single compound such as tricalcium phosphate (which substantially corresponds to hydroxyapatite, $Ca_5(PO_4)_3OH$ or $3Ca_3(PO_4)_2 \cdot Ca(OH)_2$), bone meal or dicalcium phosphate (dihydrate or anhydrous). In solution, particularly in the presence of fluoride ions, formation of hydroxyapatite, fluorohydroxyapatite and fluorapatite occurs.

Examples of other normally water-soluble or normally water-insoluble (but soluble at pH of about 6 or less) sources of calcium ion, but not phosphate ion, which can be used in the remineralizing solution of the invention include calcium salts with acetate, gluconate, nitrate, stearate, lactate, formate, molybdate, tungstate, sulfate, alkyl sulfonate (e.g., lauryl sulfonate), oleate, tartrate, sorbate, iodate, silicate, aluminate, benzoate, citrate, fumarate, butyrate, isobutyrate, malate, maleate, propionate, valerate and the like. Mixtures of such calcium sources with each other or with calcium phosphate may be employed.

Examples of sources of phosphate ion, but not calcium ion, which can be used in the remineralizing solution of the invention include the normally water-soluble or normally water-insoluble (but soluble at pH of about 6 or less) salts including alkali metal (e.g., sodium and potassium), ammonium, magnesium, barium and strontium orthophosphates and acid orthophosphates, metaphosphates, pyrophosphates, as well as glycerophosphates, fructose-6-phosphate, sorbitol-6-phosphate, glucose-1-phosphate, glucose-6-phosphate and the like. Mixtures of such phosphate sources with each other or with calcium phosphate may be employed.

Tricalcium phosphate or the other sources of calcium and phosphate which together form hydroxyapatite in solution are employed with the mole ratio of calcium ion to phosphate ion being from about 0.01 to about 100:1, typically about 0.2 to about 5:1, preferably about 1.2 to about 2:1, e.g., about 1.4 to about 1.7:1. A ratio of calcium to phosphate of 1.67:1 corresponds to the ratio of calcium to phosphate in dental enamel. The amount of calcium ion and phosphate ion in the solution is sufficient to effect remineralization, there being typically at least about 50 ppm ($5 \times 10^{-}M$) of each calcium ion and phosphate ion. The maximum amount of calcium ion and phosphate ion desirable is that which would not result in precipitate formation. This could vary depending on the ion sources and the pH conditions. Typically, about 35,000 ppm of calcium ion and about 40,000 ppm of phosphate can be employed and precipitation still avoided.

In the prior art it has been difficult to maintain the solubility of calcium phosphate, particularly in the presence of a fluoride source. As previously indicated, this is overcome in the present invention when the effective antinucleating agents are employed. Examples of fluoride ion sources (including complex fluoride ions) include alkali metal (e.g., sodium, potassium and lithium) ammonium, alkaline earth metal (e.g., calcium, barium, strontium, magnesium), aluminum, zinc, stannous, indium, zirconium, copper, nickel, palladium and organonitrogen such as alkylamine (e.g., hexylamine) compounds with fluoride ion sources. Sources of fluoride ions include fluoride, fluorophosphate (including monofluorophosphate, difluorophosphate and polyflurorphosphate), silicofluoride, fluorozirconate, fluoroborate and fluorostannite. Typical compounds are sodium fluoride, zinc fluoride, stannous fluoride and sodium monofluorophosphate. Sodium fluoride and sodium monofluorophosphate are preferred. The fluoride source compound is desirably present in amount to provide about 1 ppm to 10,000 ppm (0.0001%–1%) fluoride to the remineralizing solution, e.g., about 1 ppm to 1000 ppm (0.0001–0.76%) sodium monofluorophosphate, preferably about 5 ppm fluoride. The amount of the compound employed should not be sufficient to result in precipitate formation. For instance, in the case of a fluoride source of low solubility, such as calcium fluoride, the amount of the compound employed should not exceed 1500 ppm.

The stable remineralizing solution is prepared by adding the calcium ion and phosphate ion sources to water and lowering the pH to keep the solution clear. The ion sources may be a single material, such as tricalcium phosphate or may be a plurality of materials, such as calcium chloride and sodium dihydrogen orthophosphate. The ratio of calcium ion to phosphate ion may be from about 0.01 to about 100:1, but is desirably about 1.67:1 in order to optimally form hydroxyapatite, for instance using about 1.5mM calcium ion and 0.9mM phosphate ion in solution. A preservative such as sodium benzoate or methyl-4-hydroxybenzoate may be employed to reduce bacterial growth. An electrolyte salt as an alkali metal (e.g., sodium or potassium) chloride may be present (e.g., 1 to 1000 ppm) in the stable remineralizing solution to further improve stability and diffusion of remineralizing material into subsurface lesions.

Acidic materials are used to reduce the pH to about 2–4, typically about 2.8–3.8, in order to maintain clarity of the solution. Typical materials include phosphoric acid, hydrochloric acid and the like.

The pH is then raised to a mildly acid level, such as about 5 to 6.5, e.g., about 6, with basic materials such as sodium hydroxide, potassium hydroxide, ammonium hydroxide and the like.

The solution can then be stabilized against precipitation by incorporating therein an effective antinucleating agent, such as ethylene diamine tetramethylenephosphonic acid, pentasodium salt. The antinucleating agent is added to the solution in amount of about $1 \times 10^{-6}M$ to $1 \times 10^{-4}M$, typically about $3 \times 10^{-4}M$ (300 ppm) and thoroughly mixed therein.

The pH can then be maintained or even raised to about 9, with the effective antinucleating agent preventing precipitation of hydroxyapatite. Preferably it is raised to a physiological pH in the range of about 6.8–7.5, typically about 7 to 7.5. Basic materials of the type indicated may be employed to raise the pH.

A fluoride ion source such as sodium fluoride or sodium monofluorophosphate is then added in the indicated amount and the solution can be diluted to a desired concentration. In the solution of the present invention the fluoride does not cause the hydroxyapatite to precipitate.

Thus, the solution can be maintained for a long period of time, remaining effective when brought into contact with dental material to remineralize sub-surface lesions. The solution can be used as such or incorporated into dental compositions, such as mouth rinse.

The solution of the invention may be applied to dental surfaces as such, for instance, by rinsing the mouth therewith or it may be incorporated into a mouthwash.

When incorporated into a mouthwash, the solution is typically about 20-80% by weight of the mouthwash, which mouthwash also includes a non-toxic lower aliphatic alcohol, such as ethanol, n-propanol or isopropanol. A surface active agent (e.g., about 1-5%) such as sodium lauryl sulfate, sodium N-lauroyl sarcosinate or polyoxyethylene-polyoxypropylene (Pluronic) material, a flavoring and/or sweetening material or antibacterial agent may also be present.

When incorporated into a dental cream or gel, the solution is typically about 20-60% by weight of the cream or gel; such cream or gel also typically includes about 10-50% of a dentally acceptable polishing material such as a water insoluble phosphate (e.g., insoluble sodium metaphosphate, dicalcium phosphate, tricalcium phosphate or trimagnesium phosphate), calcium carbonate, or silica (colloidal, precipitated or crystalline). The dental cream also generally contains humectant such as glycerine, sorbitol, propylene glycol or polyethylene glycol 400 and gelling agent such as sodium carboxmethyl cellulose or Irish Moss. Also, surface active agent flavoring and/or sweetening material, antibacterial agent, antibacterial preservative, (e.g., sodium benzoate or methyl-4-hydroxy benzoate), silicone material, chlorophyll compound or ammoniated material may be present.

The following examples illustrate the invention but do not limit it. All parts, amounts and proportions are by weight unless otherwise noted.

EXAMPLE 1

A stock solution of hydroxyapatite (tricalcium phosphate) is prepared by adding hydroxyapatite to water to a final concentration of 1.5mM calcium and 0.9mM phosphate. 0.25 grams of sodium benzoate (from 0.05% solution thereof) are then added to the solution to minimize bacterial growth.

Phosphoric acid is then added to 500 ml of the stock solution to produce a clear solution at pH 3, after which the pH is raised to 6 with 1 N potassium hydroxide. Next EDITEMPA is added and mixed into the solution to a concentration of $1 \times 10^{-5}$M thereof, following which additional potassium hydroxide is added to produce a pH of 7. Sodium monofluorophosphate is then added to a concentration of 5 ppm fluoride in the stock solution following which sodium chloride is added to give an electrolyte concentration of 50mM and additional water is added to 1 liter.

The solution thus formed remains stable and clear upon storage. A similar solution without EDITEMPA and without fluoride containing compound results in precipitation by 10 seconds from the time of the final pH rise. When the fluoride containing compound is present and EDITEMPA absent, precipitation also occurs by 10 seconds from the time of the final pH rise. The solution remains clear when just sodium chloride is omitted.

EXAMPLE 2

Example 1 with EDITEMPA and sodium monofluorophosphate is repeated using dicalcium phosphate dihydrate in place of hydroxyapatite to give a final concentration of 60 ppm calcium and 400 ppm phosphate in the stock solution. The solution remains stable and clear.

EXAMPLE 3

Example 1 with EDITEMPA and sodium monofluorophosphate is repeated except that in place of hydroxyapatite, calcium chloride and sodium phosphate are each added to water to form the stock solution with a final concentration of 60 ppm calcium and 400 ppm phosphate. The solution remains stable and clear.

EXAMPLE 4

Each of Example 1,2 and 3 are repeated except that in place of EDITEMPA, there is separately employed PAA (concentration $5 \times 10^{-3}$M); PODP (concentration $5 \times 10^{-4}$M); UniRoyal Oligomer ND-2 (concentration $5 \times 10^{-4}$M). All solutions remain stable and clear.

EXAMPLE 5

100 parts of each solution of Examples 1-4 are incorporated into 100 parts of the following mouthwash:

|  | PARTS |
|---|---|
| Ethanol | 6 |
| Pluronic F-10 8 (polyoxyethylene-polyoxypropylene) | 2 |
| Glycerine | 15 |
| Benzoic acid | 0.01 |
| Sodium Saccharin | 0.02 |
| Flavor | 0.075 |
| Sodium benzoate | 0.500 |
| Color | 0.0006 |
| Water | Q.S. to 100 |

It will be apparent to one skilled in the art that various modifications of the foregoing Examples may be made thereto.

We claim:

1. A stable aqueous remineralizing solution comprising water having dissolved therein a source of calcium ions and a source of phosphate ions, the amount of calcium ions and phosphate ions being sufficient to effect remineralization of dental enamel; a compound which provides fluoride anticaries agent; and an antinucleating agent selected from the group of acids and orally acceptable water-soluble salts thereof consisting of: diamine tetramethylenephosphonic acids of the formula $(M_2O_3PH_2C)_2N(CH_2)_nN(CH_2PO_3M_2)_2$, wherein n is an integer from 1-10; phosphonoacetic acid or salt thereof of the formula $M_2O_3PCH_2COOM$; peroxydiphosphate of the formula $M_4P_2O_8$;

an oligomer

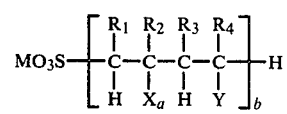

in which M is hydrogen
or an orally acceptable cation: $R_1$, $R_2$, $R_3$, and $R_4$ are independently hydrogen, methyl or ethyl; Y is at least one hydrophilic member of the group consisting of —COOM, —CONH$_2$ and CH$_2$OH; X is at least one hydrophobic member of the group consisting of —CN, —COOR, —COOR$_5$OR, —CONHR and —COONHR$_4$COR;

R is $C_{1-8}$ alkyl; $R_5$ is $C_{1-4}$ alkylene; a is 0–7 and a+b is about 4–15; said solution having a pH of about 5 to 9.

2. The stable aqueous remineralizing solution claimed in claim 1 wherein the pH of said solution is about 6.8 and 7.5.

3. The stable aqueous remineralizing solution claimed in claim 1 wherein said antinucleating agent is present in amount of about 1 to 500 ppm.

4. The stable aqueous remineralizing solution claimed in claim 1 wherein said antinucleating agent is said diamine tetramethylenephosphonic acid or orally acceptable salt thereof.

5. The stable aqueous remineralizing solution claimed in claim 4 wherein said antinucleating agent is ethylene diamine tetramethylenephosphonic acid or orally acceptable salt thereof.

6. This stable aqueous remineralizing solution claimed in claim 1 wherein said antinucleating agent is said phosphonoacetic acid or orally acceptable salt thereof.

7. The stable aqueous remineralizing solution claimed in claim 1 wherein said antinucleating agent is said an orally acceptable peroxydiphosphate.

8. The stable aqueous remineralizing solution claimed in claim 1 wherein said antinucleating agent is said oligomer or orally acceptable salt thereof.

9. The stable aqueous remineralizing solution claimed in claim 1 wherein an electrolyte salt is present.

10. The stable aqueous remineralizing solution claimed in claim 1 wherein the mole ratio of calcium to phosphate is from about 0.01 to about 100:1 and at least about 50 ppm of each of calcium and phosphate is present.

11. The stable aqueous remineralizing solution claimed in claim 10 wherein said source of calcium ions and of phosphate ions is hydroxyapatite and the mole ratio of calcium to phosphate is about 1.67 to 1.

12. The stable aqueous remineralizing solution claimed in claim 1 wherein said source of calcium ions and of phosphate ions is di calcium phosphate.

13. The stable aqueous remineralizing solution claimed in claim 1 wherein said source of calcium ions is calcium chloride and said source of phosphate ions is sodium phosphate.

14. The stable aqueous remineralizing solution claimed in claim 1 wherein said compound which provides fluoride anticaries agent provides about 1 ppm to about 1000 ppm.

15. The stable aqueous remineralizing solution claimed in claim 14 wherein said compound which provides fluoride anticaries agent is sodium monofluorophosphate.

16. A mouthwash comprising a non-toxic lower aliphatic alcohol carrier and incorporated therein the stable aqueous remineralizing solution claimed in claim 1.

17. A mouthwash as claimed in claim 16 wherein said alcohol is ethanol and said solution is about 20–80% by weight of said mouthwash.

* * * * *